United States Patent
Park et al.

(10) Patent No.: US 8,828,954 B2
(45) Date of Patent: Sep. 9, 2014

(54) USE FOR SCOPOLIN AND DERIVATIVES THEREOF

(75) Inventors: Tae Sun Park, Seoul (KR); Ha Won Kim, Seoul (KR); Wan Kyun Hwang, Seoul (KR)

(73) Assignee: Yonsei University Technology Holdings, Inc., Incheon (KR)

( * ) Notice: Subject to any disclaimer, the term of this patent is extended or adjusted under 35 U.S.C. 154(b) by 30 days.

(21) Appl. No.: 13/580,481

(22) PCT Filed: Aug. 17, 2010

(86) PCT No.: PCT/KR2010/005423
§ 371 (c)(1),
(2), (4) Date: Aug. 24, 2012

(87) PCT Pub. No.: WO2011/102577
PCT Pub. Date: Aug. 25, 2011

(65) Prior Publication Data
US 2012/0322754 A1 Dec. 20, 2012

(30) Foreign Application Priority Data
Feb. 22, 2010 (KR) .......................... 10-2010-0015532

(51) Int. Cl.
*A61K 31/70* (2006.01)
*A61K 31/37* (2006.01)

(52) U.S. Cl.
CPC ..................................... *A61K 31/37* (2013.01)
USPC ........................................................ 514/27

(58) Field of Classification Search
None
See application file for complete search history.

(56) References Cited

FOREIGN PATENT DOCUMENTS

| CN | 1615847 | * | 5/2005 |
| JP | 2004/081115 | * | 3/2004 |
| WO | WO 00/75124 | | 12/2000 |

OTHER PUBLICATIONS

Wu et al., "Bioactivity Guided Isolation of Alpha-Glucosidase Inhibitor from Whole Herbs of Crossostephium Chinense," Zhongguo Zhong Yao Za Zhi. 34:2206-2211, 2009. (Abstract only).

* cited by examiner

*Primary Examiner* — Traviss C McIntosh, III
(74) *Attorney, Agent, or Firm* — Clark & Elbing LLP (57) ABSTRACT

The present invention relates to a novel use for the compound of Chemical formula 1 in order to produce drugs or foods for the prevention or treatment of obesity, fatty liver, diabetes, metabolic syndrome or the like, and to a composition for the prevention or treatment of obesity, fatty liver, diabetes, metabolic syndrome or the like which contains the compound of Chemical formula 1 as an active ingredient, and also to a method for the prevention or treatment of obesity, fatty liver, diabetes, metabolic syndrome or the like comprising the administration of the compound of Chemical formula 1 to a mammal in a therapeutically effective dose. According to the present invention, the compound of Chemical formula 1 has been confirmed to suppress the differentiation of adipocytes, to reduce body weight and the amount of visceral fat, to reduce concentrations of cholesterol, triglycerides, free fatty acids and glucose which are associated with fatty liver and diabetes and the like and to reduce the fatty component in liver tissue, to suppress gene expression associated with obesity in visceral fatty tissue, and to increase the amount of expression of UCP1 and UCP3 which are UCP (uncoupling protein) genes involved in thermogenesis. The compound of Chemical formula 1 can be used to advantage in order to prevent or treat obesity, fatty liver, diabetes, metabolic syndrome and the like since, unlike the obesity treating agents based on synthetic drugs currently in use, it is based on a natural substance and hence entails a very low risk of adverse effects and, additionally, it exhibits its pharmacological effects by regulating the expression of genes associated with obesity rather than exhibiting pharmacological effects by acting on enzymes or the nervous system.

6 Claims, 5 Drawing Sheets

USE FOR SCOPOLIN AND DERIVATIVES THEREOF

CROSS-REFERENCE TO RELATED APPLICATIONS

This application is the U.S. national stage filing under 35 U.S.C. §371 of international application PCT/KR2010/005423, filed Aug. 17, 2010, which claims priority from Korean Patent Application 10-2010-0015532, filed Feb. 22, 2010.

FIELD OF THE INVENTION

The present invention relates to novel uses of scopolin and its derivatives.

DESCRIPTION OF THE RELATED ART

According to the 2007 Korea National Health and Nutrition Examination Survey recently reported by the Ministry of Health & Welfare, 31.7% of Korean adults turned out to be obese.

Since obesity induces complications such as fatty liver, hypertension, diabetes and cardiovascular diseases or metabolic syndrome, as well as ugly appearance such that the socioeconomic loss is becoming a serious social issue.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related adverse effects such as steatorrhea, gas generation and reduced absorption of oil-soluble vitamins. Reductil, which increases serotonin and noradrenaline levels in the sympathetic nervous system, has adverse effects such as headache, dry mouth, loss of appetite, insomnia, constipation, etc. Besides, a large number of anti-obesity drugs have been withdrawn from the market due to severe adverse effects. For example, aminophylline is reported to have various adverse effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in adverse effects and in overcoming chronic diseases, foods and drugs derived from natural sources are drawing attentions.

Scopolin[7-(beta-D-glucopyranosoyloxy)-6-methoxy-2H-1-benzopyran-2-one] contained in plants such as *Erycibe obtusifolia, Helianthus annuus, Artemisia dalailamae, Arabidopsis thaliana, Crossostephium chinense, Santolina oblongifolia, Euphorbia chrysocoma, Diodia teres, Aesculus hippocastanum, Althaea officinalis, Apium graveolens, Artemisia abrotanum, Artemisia annua, Avena sativa, Datura stramonium, Hedera helix, Hyoscyamus niger, Ipomoea batatas, Mandragora officinarum, Morus alba, Nicotiana tabacum, Scopolia carniolica, Solanum tuberosum* and *Viburnum prunifolium* is one of coumarin compounds, which is represented by the following Chemical formula 2:

[Chemical Formula 2]

Currently known physiological activities of scopolin include anti-inflammatory and anti-dementia efficacies. Silvan A M et al. have reported that scopolin from ethanol extracts of *Santolina oblongiforma* is administered into mouse intraperitoneal macrophages stimulated with ionophore, as a result, exhibiting suppression of eicosanoid release (Silvan A M, Abad M J, Bermejo P, Sollhuber M, Villar A., Antiinflammatory activity of coumarins from Santolina oblongifolia. *J Nat Prod* December; 59(12):1183-5, 1996). In addition, Rollinger J M et al. have reported that scopolin from *Scopolia carniolica* Jaqc. inhibits acetylcholine esterase to treat Alzheimer's disease and dementia (Rollinger J M, Hornick A, Langer T, Stuppner H, Prast H., Acetylcholinesterase inhibitory activity of scopolin and scopoletin discovered by virtual screening of natural products. *J Med Chem* December 2; 47(25):6248-54, 2004).

However, hitherto, scopolin and its derivatives have not been reported in use for preventing or treating obesity, fatty liver, diabetes and metabolic syndromes.

DETAILED DESCRIPTION OF THIS INVENTION

Technical Purposes of this Invention

The present invention is drawn to provide natural-derived obesity therapeutic compounds with overcoming against adverse effects.

Other features and aspects will be apparent from the following detailed description, drawings and claims.

Technical Solutions of this Invention

The present invention provides a novel use of the compound represented by the following Chemical formula 1 to prepare a pharmaceutical composition or food composition for preventing or treating obesity, fatty liver, diabetes and metabolic syndrome. The present invention provides a composition for preventing or treating obesity, fatty liver, diabetes and metabolic syndrome containing the compound represented by the following Chemical formula 1 as an active ingredient. The present invention provides a method for preventing or treating obesity, fatty liver, diabetes and metabolic syndrome, comprising administrating to a mammal a therapeutically effective amount of the compound represented by the following Chemical formula 1:

[Chemical Formula 1]

wherein, R₁ is OH, and
R₂ is H or,

R₁ and R₂ may form dioxane with their carbon atom members, wherein dioxane may be substituted with hydroxy-$C_{1-4}$ alkyl; or, $C_{1-4}$ alkoxy or hydroxy-substituted phenyl;
R₃ is H or, According to an embodiment, the compound of Chemical formula 1 is selected from the group consisting of the compounds represented by the following Chemical formulae 2-7:

[Chemical formula 2]

[Chemical formula 3]

[Chemical formula 4]

[Chemical Formula 5]

[Chemical Formula 6]

[Chemical Formula 7]

As demonstrated in the following Examples, the compound of Chemical formula 1 contributes to inhibition of adipocyte differentiation, reductions of body weight, visceral fat, cholesterol level, triglyceride level, free fatty acid level, glucose level and liver tissue lipid level. It also contributes to inhibition of obesity-related gene in visceral fat tissue and to increase of expression level for UPC1 and UCP3 involving thermogenesis. Therefore, the compound of Chemical formula 1 may be used as active ingredients in the composition for preventing or treating a disease selected from the group consisting obesity, fatty liver diabetes and metabolic syndrome.

Unlike synthetic obesity therapeutics currently being used, the compound represented by Chemical formula 1 of derived from natural source may be very low risk of adverse and useful for the prevention or treatment in obesity, fatty liver, diabetes or metabolic syndrome by regulating expressions of obesity-relating genes rather than acting on enzymes or nervous system.

The compound of Chemical formula 1 used as active ingredients in the present invention may be contained in an extract of a plant or its fraction; or contained in an isolated from or chemically-synthesized form.

The examples of plants containing the compound of Chemical formula 1 includes, but not limited to, *Erycibe obtusifolia, Helianthus annuus, Artemisia dalailamae, Arabidopsis thaliana, Crossostephium chinense, Santolina oblongifolia, Euphorbia chrysocoma, Diodia teres, Aesculus hippocastanum, Althaea officinalis, Apium graveolens, Artemisia abrotanum, Artemisia annua, Avena sativa, Datura stramonium, Hedera helix, Hyoscyamus niger, Ipomoea batatas, Mandragora officinarum, Morus alba, Nicotiana tabacum, Scopolia carniolica, Solanum tuberosum* and *Viburnum prunifolium*.

According to an embodiment, wherein the compound represented by Chemical formula 1 is contained in an extract of a plant or its fraction; wherein the plant is one or more selected from the group consisting of *Erycibe obtusifolia, Helianthus annuus, Artemisia dalailamae, Arabidopsis thaliana, Crossostephium chinense, Santolina oblongifolia, Euphorbia chrysocoma, Diodia teres, Aesculus hippocastanum, Althaea officinalis, Apium graveolens, Artemisia abrotanum, Artemisia annua, Avena sativa, Datura stramonium, Hedera helix, Hyoscyamus niger, Ipomoea batatas, Mandragora officinarum, Morus alba, Nicotiana tabacum, Scopolia carniolica, Solanum tuberosum* and *Viburnum prunifolium* in the composition.

The Examples described below illustrates the isolation process of scopolin from *Erycibe obtusifolia* but the scope of the present invention is not limited to or by the Examples. It would be understood that the compound represented by Chemical formula 1 may be isolated from the plants illustrated above or chemically synthesized in accordance with methods known to those of skill in the art.

Besides the compound of Chemical formula 1, the composition may be used along with pharmacological active ingredient which is known to have anti-obesity and anti-diabetes. For example, the composition of the present invention may further comprise ingredient which is one or more selected from Sesquiterpene derivatives, Juniperanol, *Cupressus* extract, *Juniperus chinensis* extract and *Pterocarpus santalinus* extract.

According to an embodiment, the composition of the present invention is provided a pharmaceutical composition or a food composition comprising the compound of Chemical formula 1 as an active ingredient.

The pharmaceutical composition of the present invention may be prepared using adjuvant which is suitable pharmaceutically and acceptable physiologically, in addition to the above-described active ingredient; wherein adjuvant may be used diluting agent, disintegrating agent, sweetener, bonding agent, coating material, inflating agent, lubricant, slip modifier or fragrance.

For administration, in addition to the above-described active ingredient, the composition of the present invention may further include one or more pharmaceutically acceptable carrier to provide a pharmaceutical composition.

The formulation of the pharmaceutical composition may be granule, dust, tablet, coated tablet, capsule, suppository, liquid medicine, syrup, succus, suspension, emulsion, medicinal drops or injectable liquid.

For example, for the tablet or capsule formulation, the active ingredient may be combined with a pharmaceutically acceptable carrier such as ethanol, glycerol, and water which may be administrated orally and non-toxic. In addition, if desired or necessary, suitable bonding agents, lubricants, disintegrating agents, colorants or their combination may be included. Suitable bonding agents include, but not limited to, natural sugars such as starch, gelatin, glucose or beta-lactose, corn sweetener, natural and synthetic gum such as acacia, tragacanth or sodium olate, sodium stearate, magnesium stearate, sodium benzoate, sodium acetate, sodium chloride or the like. Disintegrating agents include, but not limited to, starch, methyl cellulose, agar, bentonite, xanthan gum or the like.

For the composition in the form of a liquid solution, a pharmaceutically acceptable carrier may include saline, sterile water, Ringer's solution, buffered saline, albumin injection solution, dextrose solution, maltodextrin solution, glycerol, ethanol and mixture thereof. Also, if necessary, conventional additives such as antioxidants, buffers and bacteriostatic agents may be further added. In addition, it may be formulate to injectable formulation such as aqueous solution, suspension and emulsion, pill, capsule, granule or tablet by further adding to diluent agent, dispersing agent, surface active agent, bonding agent and lubricant.

Furthermore, the composition of the present invention may be preferably formulated depending on disease or component using method which is disclosed as suitable method in Remington's Pharmaceutical Science, Mack Publishing Company, Easton Pa.

The present invention provides a food composition for preventing or treating disease, comprising the compound of Chemical formula 1 as an active ingredient; wherein the disease is one or more selected from the group consisting obesity, fatty liver diabetes and metabolic syndrome.

The food composition according to the present invention may be formulated by same manner of the pharmaceutical composition to use for functional food or to add for various foods. The addable foods for the composition of present invention include beverages, alcoholic beverages, confectionery, diet bar, dairy products, meat, chocolate, pizza, noodles, other noodles, chewing gum, ice cream, vitamin complexes and health supplement foods.

For example, when the food composition of the present disclosure is prepared as a drink, it may further comprise, in addition to the compound of Chemical formula 1 or plants extract or its fraction containing the compound of Chemical formula 1 of the present disclosure, citric acid, high-fructose corn syrup, sugar, glucose, acetic acid, malic acid, fruit juice, various plants extract solution or the like.

The present invention provides a health functional food comprising the composition for preventing or treating disease; wherein the disease is one or more selected from the group consisting obesity, fatty liver diabetes and metabolic syndrome. The health functional food means a food having specific beneficial effects in terms of health, prepared in such a manner that the compound of Chemical formula 1 or a plant extract or its fraction containing the compound of Chemical formula 1 is added to food ingredients to provide a food such as drinks, teas, spices, chewing gum and confectionery, or to provide capsule, powder or suspension. Unlike to drugs, the health functional food has advantages in which there are no adverse effects typically caused by long-term administration of drugs. The health functional food of the present invention is very useful because it may be ingested daily. A suitable amount of the compound of Chemical formula 1 or a plant extract or its fraction containing the compound of Chemical formula 1 may be varied in the health functional food depending on its type. It may be added in an amount not to deteriorate taste of foods, generally 0.01% to 50% by weight, preferably 0.1% to 20% by weight. Also, foods in form of granule, tablet or capsule can be added commonly from 0.1% to 100% by weight, preferably 0.5% to 80% by weight. In one embodiment, the health functional food composition is in the form of a drink.

In addition, the present invention provides a use of the compound represented by the following Chemical formula 1 to prepare a pharmaceutical composition or food composition for preventing or treating disease; wherein the disease is one or more selected from the group consisting obesity, fatty liver diabetes and metabolic syndrome. As described herein, the compound of Chemical formula 1 of the present invention can be used as use for preventing or treating disease; wherein the disease is one or more selected from the group consisting obesity, fatty liver diabetes and metabolic syndrome.

Also, the present invention provides a method for preventing or treating obesity, fatty liver, diabetes or metabolic syndrome, comprising administrating to a mammal a therapeutically effective amount of a composition comprising a compound represented by the following Chemical formula 1.

The term used herein "mammal" refer to mammal to be treat, observe or experiment as subject, preferably human.

The term used herein "therapeutically effective amount" means that the amount of the active ingredient or the pharmaceutical composition sufficient to induce biological or medical responses in tissues, animals or human evaluated by researchers, veterinarians, medical doctors or clinical doctors, including the amount sufficient to alleviate diseases or disorders to be treat. It is obvious to one skilled in the art that appropriate administration dosage and administration number for active ingredients of the present disclosure may be changed depending on effect to be required. Therefore, an appropriate administration dosage may be determined by one skilled in the art and regulated variously depending on such factors as type of disease, severity of disease, content of active ingredients and other ingredients contained in composition, type of formulation, age of a patient, body weight of a patient, health state of a patient, gender of a patient, diet of a patient, administration time, administration route, excretion rate of composition, administration period, drug used simultaneously. In the treatment method of the present invention, preferably, dosage of the composition of the present disclosure may be 1 mg/kg-250 mg/kg in case of adult.

In the treatment method of the present invention, the composition of the present disclosure may be administrated with conventional manners through oral, rectal, intravenous, arterial, intraperitoneal, intramuscular, intrasternum, transdermal, topical, intraocular or intradermal route.

The present invention will now be described in further detail by examples. It would be obvious to those skilled in the art that these examples are intended to be more concretely illustrative and the scope of the present invention as set forth in the appended claims is not limited to or by the examples.

Advantageous Effects of this Invention

In according to the present invention, the compound of Chemical formula 1 contributes to inhibition of adipocyte differentiation, reductions of body weight, visceral fat, cholesterol level, triglyceride level, free fatty acid level, glucose level and liver tissue lipid level. It also contributes to inhibition of obesity-related gene in visceral fat tissue and to increase of expression level for UPC1 and UCP3 relating thermogenesis. Unlike synthetic obesity therapeutics currently being used, the compound represented by Chemical formula 1 of derived from natural source may be very low risk of adverse and useful for the prevention or treatment in obesity, fatty liver, diabetes or metabolic syndrome by regulating expressions of obesity-relating genes rather than acting on enzymes or nervous system.

PREFERRED EXAMPLES OF THIS INVENTION

EXAMPLES

Example 1

Isolation of Scopolin from *Erycibe obtusifolia*

20 kg of *Erycibe obtusifolia* was powdered and extracted using ethanol to obtain the ethanol extract 1.45 kg (yield:

7.25%). The resultant was dissolved in water and fractionated using hexane, methylene chloride, ethylacetate and water. 420 g of the water fraction (yield: 2.1%) was adsorbed onto a non-ionic porous resin Amberliet XAD-4 and desorbed with $H_2O$, 50% MeOH and MeOH. Then, 65.1 g of the 50% MeOH extract containing scopolin (yield: 0.33%) was subjected to a column chromatography using Sephadex LH-20 gel and 30% MeOH solvent to obtain 4.5 g of scopolin (yield: 0.02%).

Example 2

Confirmation of Inhibitory Effects of Scopolin on Adipocytes Differentiation in Mouse Adipocyte Cell Line 3T3-L1

Mouse adipocyte cell line (3T3-L1) was used to investigate the effect of scopolin on differentiation and growth of adipocytes. The preadipocytes, 3T3-L1 cells, were seeded on a 12-well plate and cultured to confluency using Dulbecco's modified Eagle's medium (DMEM) containing 1% penicillin-streptomycin, 1% non-essential amino acid and 10% fatal bovine serum (FBS), in a 5% CO2 incubator at 37° C. The 3T3-L1 cells grown to confluency were cultured for 2 days in MDI medium containing 0.5 mM isobutylmethylxanthine, 1 µM dexamethasone and 1 µg/mL insulin to differentiate them into differention adipocytes. Then, the cells were further cultivated in DMEM containing 1 µg/mL insulin to differentiate them into mature adipocytes. The cells were further cultured for 10 more days while replacing DMEM every other day to obtain fully differentiated adipocytes.

From the first day when MDI was added to the 3T3-L1 cells, scopolin was treated at concentrations of 0.1, 1, 10, 50 and 100 µM with 2-day intervals. Scopolin was used after being dissolved in DMSO. Only DMSO was added to the negative control group. After culturing for a total of 14 days, the medium was removed when the differentiation was completed and lipid droplets in the differentiated adipocytes were stained. For this, the cells were washed twice with phosphate buffered saline (PBS), fixed in 10% buffered neutral formalin (BNF) for 1 hour, washed once again with PBS, stained for 1 hour by adding 1 mL of Oil Red O dye, which specifically stains fat red, on the 12-well plate, and washed twice with distilled water. In order to measure the level of triglyceride contained in the differentiated 3T3-L1 cells, the stained lipid droplets were dissolved in 1 mL of isobutanol and optical density (OD) value was measured at 600 nm.

Figure 1:
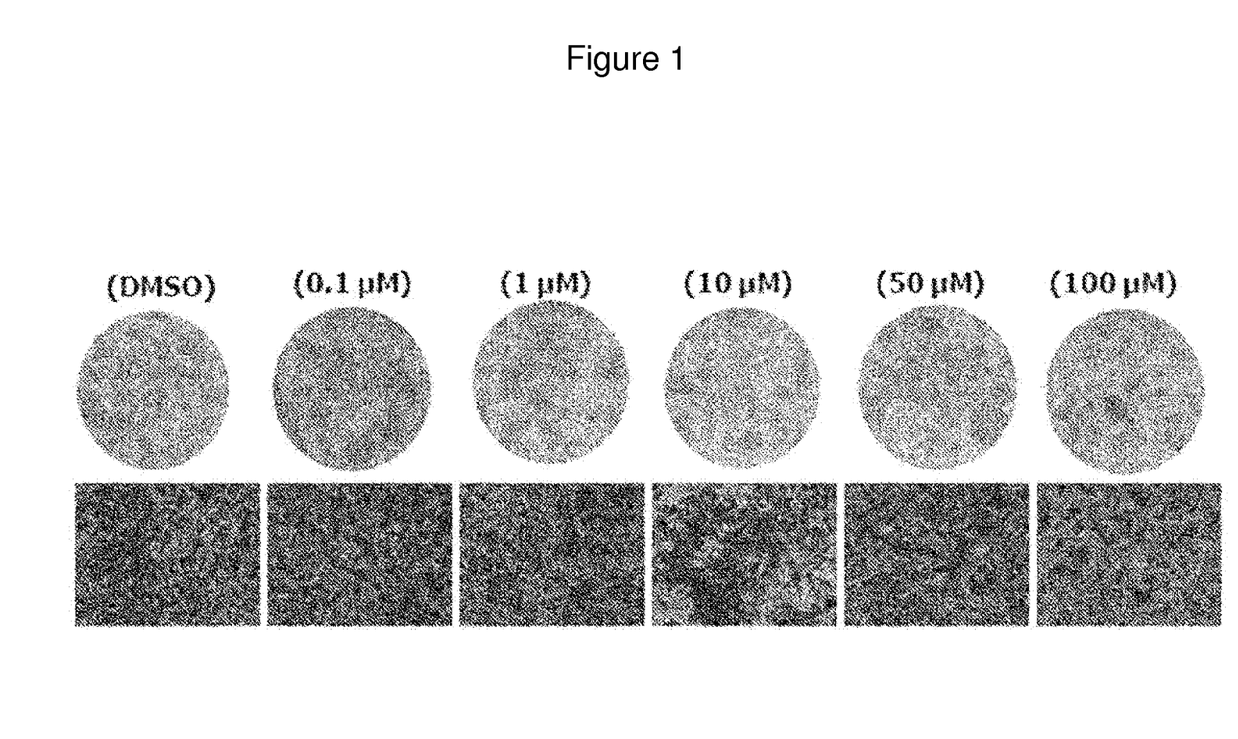
FIG. 1 is image stained by Oil-red in preadipocytes with scopolin treatment, in which it represents that scopolin reduced the differentiation of the preadipocytes in a concentration-dependent manner.

As a result, it has verified that scopolin reduced the differentiation of the preadipocytes in a concentration-dependent manner as shown in FIG. 1.

Example 3

Confirmation of Decrease Effect of Scopolin on Body Weight and Visceral Fat in Mouse The obesity-inducing control diet used in the present test was high-fat diet (HFD: 40% fat calorie, 17 g lard+3% corn oil/100 g diet). Diets supplemented with scopolin had the same composition as HF, except that each derivative was included at 0.02%. The diabetic drug metformin was added at 0.1% or the hyperlipidemic drug atorvastatin was added at 0.01% to HFD as controls. The normal diet (ND) was prepared according to the AIN-76 rodent diet composition (American Institute of Nutrition, Report of the American Institute of Nutrition ad hoc committee on standards for nutritional studies. J. Nutr., 107: 1340-1348, (1977)) (Table 1).

TABLE 1

Compositions of test diets

| Ingredients | Normal diet (ND) (g/kg diet) | High-fat diet (HFD) (g/kg diet) | Scopolin-supplemented diet (SPID)(g/kg diet) |
|---|---|---|---|
| Casein | 200 | 200 | 200 |
| D/L-Methionine | 3 | 3 | 3 |
| Corn starch | 150 | 111 | 110.8 |
| Sucrose | 500 | 370 | 370 |
| Cellulose | 50 | 50 | 50 |
| Corn oil | 50 | 30 | 30 |
| Lard | — | 170 | 170 |
| Vitamin complex | 10 | 12 | 12 |
| Mineral complex | 35 | 42 | 42 |
| Choline bitartrate | 2 | 2 | 2 |
| Cholesterol | — | 10 | 10 |
| Tert-butylhydroquinone | 0.01 | 0.04 | 0.04 |
| scopolin | — | — | 0.2 |
| Total (g) | 1,000 | 1,000 | 1,000 |
| Fat (% calorie) | 11.5 | 39.0 | 39.0 |
| Total calorie (kJ/kg diet) | 16,439 | 19,315 | 19,315 |

5-week-old male C57BL/63 mice (Orient, Korea) were accustomed to the laboratory environment for 1 week while feeding solid feed. Then, they were randomly divided into high-fat diet and test groups and bred for a total of 10 weeks. The diet was given between 10 and 11 a.m. every day together with water. Food intake was measured every day and body weight was measured once a week. In order to avoid transient body weight increase after feed intake, body weight was measured 2 hours after removing the feed. All numerical values are represented as mean±SEM of values obtained from eight mice, and significances showed with $P<0.001$ level according to Duncan's multiple range test by one-way ANOVA.

Figure 2:
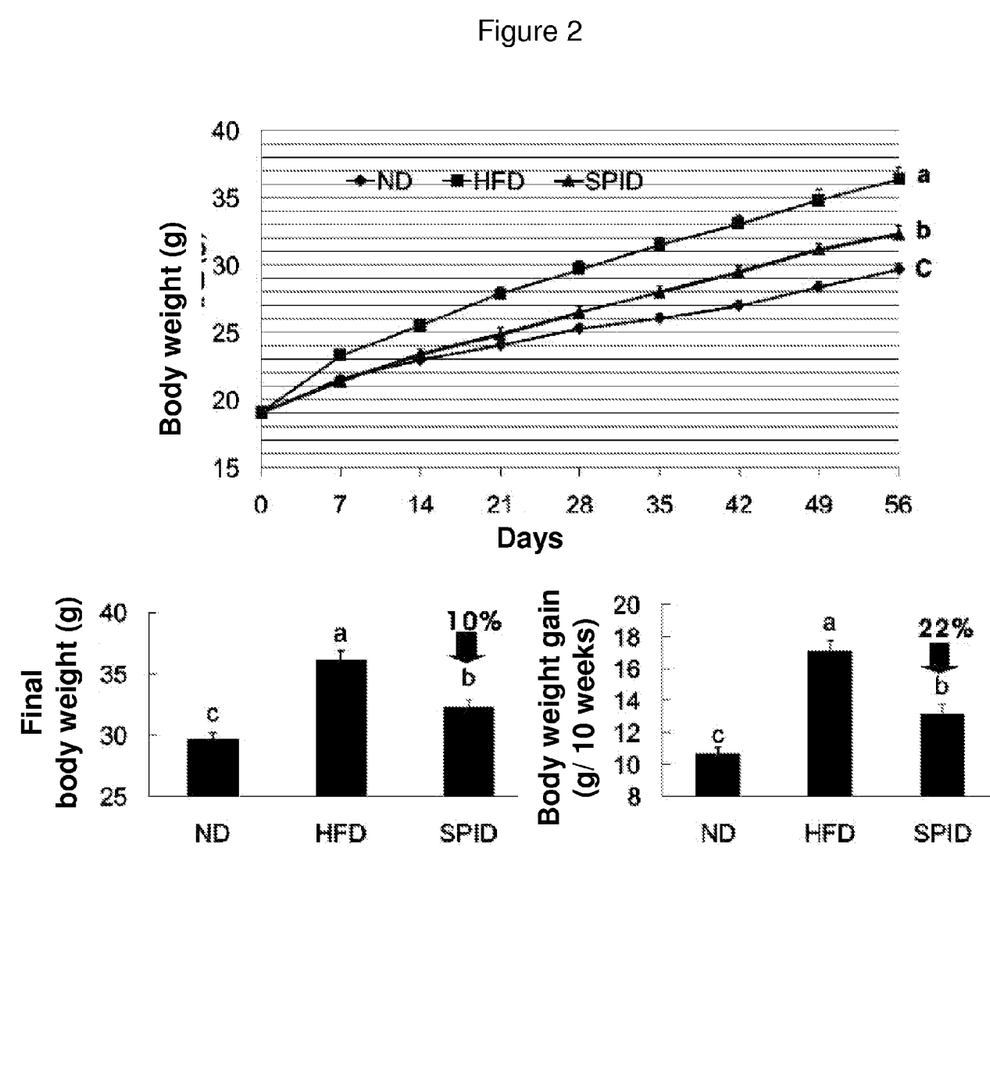
FIG. 2 indicates a graph expressed mice final body weight and body weight gain in normal diet (ND), high-fat diet (HFD), scopolin-supplemented group during 10 weeks of breeding.

As a result, after feeding the test diet for 10 weeks, the scopolin-supplemented group showed significant decrease of final body weight by 10% and the cumulative body weight gain by 22% as compared to HFD, as shown in FIG. 2.

After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes for the separation of plasma.

Figure 3:
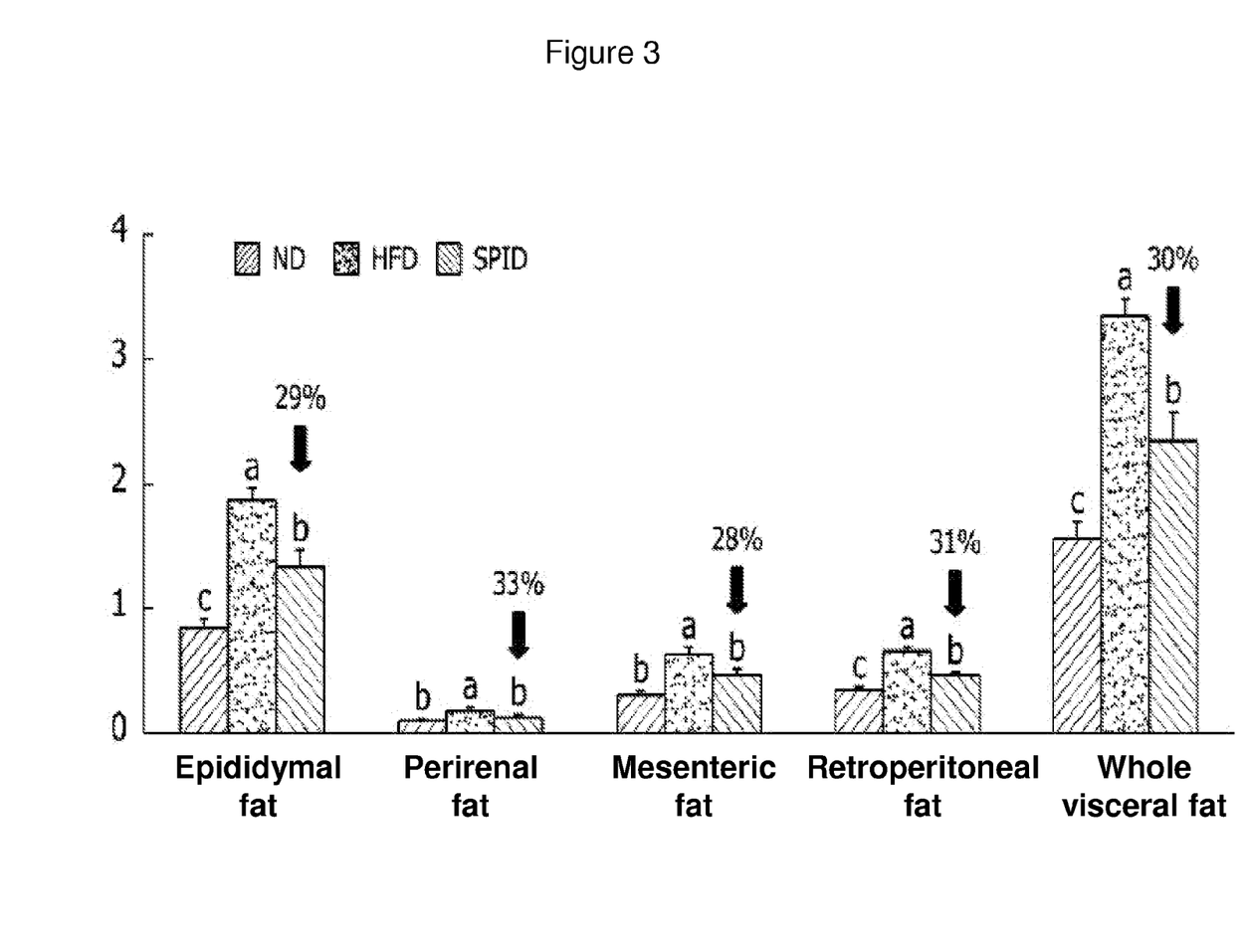
FIG. 3 indicates a graph expressed mice visceral fat weight in normal diet (ND), high-fat diet (HFD), scopolin-supplemented group during 10 weeks of breeding.

As a result, the scopolin-supplemented group (SPID) showed significantly reduced weights of the epididymal (by 29%), perirenal (by 33%), mesenteric (by 28%), and retroperitoneal (by 31%) fat-pads as compared to the control group (HFD) and the total visceral fat weight was significantly reduced by 30% in the SPID group than in the HFD group as shown in FIG. 3 ($P<0.001$). Accordingly, it would be appreciated that socopolin has excellent effects to reduce body weights and visceral fat-pad weights.

Example 4

Confirmation of Prevention and Treatment Effect of Scopolin on Hyperlipidemia, Fatty Liver and Diabetes After 10 weeks of breeding, total cholesterol, HDL-cholesterol, triglyceride and glucose levels in the plasma and lipid levels in the liver tissue were measured as follows: Total cholesterol, HDL-cholesterol, triglyceride, free fatty acid and glucose levels in the plasma were measured twice for each using a commercially available kit (Bio Clinical System). The level of LDL+VLDL in plasma was calculated by subtracting HDL level from the total cholesterol level. The activities of ALT (alanine aminotransferase) and AST (aspartate aminotransferase) used as liver function indicator were measured using a commercially available kit (Bio Clinical System, Korea).

In addition, lipids were extracted from the liver tissue according to Folch et al.'s method (Folch J, Lees M, Sloane Stanley G H. A simple method for the isolation and purification of total lipides from animal tissues. J Biol. Chem. 1957; 226:497-509). After adding 1 mL of distilled water to 0.25 g of the liver tissue, the liver tissue was homogenized using a Polytron homogenizer (IKA-Werke GmbH & Co., Ultra-Turrax, Staufen, Germany). After adding 5 mL of chloroform: methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed. The commercially available kits (Bio Clinical System, Korea) were used to measure the levels of triglyceride, cholesterol and free fatty acids of the liver tissue.

TABLE 2

The levels of lipid and glucose in the blood of mice with scopolin-supplemented group

|  | Normal diet group (ND) | High-fat diet group (HFD) | scopolin-supplemented diet group (SPID) |
|---|---|---|---|
| Triglyceride (mmol/l) | 0.59 ± 0.04[b] | 0.90 ± 0.01[a] | 0.65 ± 0.07[b] |
| Total cholesterol (mmol/l) | 3.63 ± 0.15[c] | 6.57 ± 0.13[a] | 5.07 ± 0.26[b] |
| LDL + VLDL cholesterol (mmol/l) | 2.29 ± 0.12[c] | 5.52 ± 0.14[a] | 3.88 ± 0.27[b] |
| Free fatty acid (µEq/g) | 572 ± 42.8[b] | 869 ± 14.9[a] | 635 ± 65.6[b] |
| Glucose (mmol/l) | 7.10 ± 0.27[b] | 8.97 ± 0.63[a] | 7.51 ± 0.32[b] |

TABLE 3

The levels of liver weight, lipid and liver function in liver of mice with scopolin-supplemented group

|  | Normal diet group (ND) | High-fat diet group (HFD) | scopolin-supplemented diet group (SPID) |
|---|---|---|---|
| Liver weight (g) | 1.3 ± 0.11[b] | 2.2 ± 0.22[a] | 1.7 ± 0.14[b] |
| Triglyceride (µmol/g) | 27.6 ± 1.67[c] | 70.9 ± 3.71[a] | 55.6 ± 5.3[b] |
| Cholesterol (µmol/g) | 33.9 ± 0.83[c] | 130.2 ± 8.78[a] | 102.9 ± 5.4[b] |
| Free fatty acid (µEq/g) | 16.1 ± 0.89[c] | 49.8 ± 2.04[a] | 33.6 ± 4.6[b] |
| ALT (alanine aminotransferase) (IU/L) | 7.22 ± 0.39[b] | 10.43 ± 0.64 | 5.55 ± 0.78[b] |
| AST (aspartate aminotransferase) (IU/L) | 7.29 ± 0.41[b] | 9.90 ± 0.62[a] | 5.80 ± 0.43 |

As a result, the scopolin-supplemented group showed significantly lower plasma levels of triglyceride (by 28%), total cholesterol (by 23%), LDL+VLDL cholesterol (by 30%) and free fatty acid (by 27%) as compared to the HFD group, as shown in table 2. Moreover, scopolin supplemented to the HFD resulted in a significant reduction of the fasting blood sugar level by 16%, as compared to HFD. Accordingly, it could be recognized that scopolin has the excellent effects of improving hyperlipidemia and insulin resistance in obesity induced by the HFD.

In addition, as shown in Table 3, after feeding the test diet for 10 weeks, absolute weight of liver (g) in the scopolin-supplemented group (SPID) was significantly reduced by 23%, as compared to the HFD group. The scopolin-supplemented group showed significantly decreased levels of triglyceride (by 22%), cholesterol (by 21%) and free fatty acid (by 33%) in liver tissue as compared to HFD. Moreover, the HFD group exhibited significantly higher plasma activities of ALT (alanine aminotransferase) and AST (aspartate aminotransferase), which are parameters for hepatic function, as compared to the normal diet group and the SPID group showed significantly decreased plasma activities of ALT (by 46%) and AST (by 41%) as compared to the HFD group.

Accordingly, it could be recognized that scopolin has the excellent effects of ameliorating fatty liver and hepatic function parameters in obesity induced by the HFD.

The numerical values in table 2 and 3 are represented as mean±SEM of values obtained from eight mice. The characters above the bars indicate significant difference among dietary groups by one-way analysis of variance (ANOVA) test and Duncan's multiple range test ($P<0.05$).

Example 5

Inhibitory Effect of Obesity-Related Gene Expressions in Mouse Visceral Fat Tissues by Scopolin Adipogenesis is a process in which preadipocytes are proliferated and differentiated to adipocytes, which is accompanied with changes of cell morphology and gene expression profiles. In adipogenesis, lipids are accumulated and adipocyte-specific genes such as aP2 (fatty acid binding protein), LPL (lipoprotein lipase) and adipsin are expressed under controls of three transcription factors including PPARγ (Peroxisome proliferator activated receptor gamma), C/EBPs (CCAAT enhancer-binding proterins) and SREBP-1c (sterol regulatory binding protein-1c).

Meanwhile, the dysfunction of mitochondria is related to senescence, heart diseases and gastrointestinal, endocrine and neurological disorders. The damages of the oxidation process in mitochondria increase glucose production in liver tissues and hyperglycemia, finally causing fatty liver. The mitochondria forms proton gradient across its inner and outer membranes by the electron transport chain, and generates ATP through F0F1-ATPase using the proton gradient as a driving force. Where F0F1-ATPase is not normally worked, the proton gradient disappears through uncoupling proteins to generate heat. In current, it has been reported that UCPs in adipose tissues promotes thermogenesis with maintaining redox balance by the energy-dissipatory mechanism. Therefore, UCPs as well as AMPK (AMP-activated protein kinase) become highlighted as novel targets for obesity treatment.

Accordingly, to identify that scopolin inhibits directly obesity-related gene expressions, the inventors examined whether obesity-related gene is expressed according to scopolin treatment through RNA was isolated from epididymal fat tissues obtained in the example 3 and performed RT-PCR.

First, after adding 1 mL of Trizol agent per 0.1 g of epididymal fat tissues, the mixture was homogenized and centrifuged at 12,000×g for 10 min at 4° C. The supernatant was transferred to a new tube and 200 µl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA concentration of sample was measured at a wavelength of 260 nm and 280 nm using a UV/VIS spectrophotometer (Beckman coulter, DU730) and the integrity of RNA sample was verified by agarose gel electrophoresis.

The RNA sample obtained from the epididymal fat tissues was trasnscribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 4. The amplified products (1 μl) were resolved on 1% agarose gel electrophoresis.

TABLE 4

Primer sequences for RT-PCR

| Gene | Primer | Sequence(5'→3') | Anealing Temp (° C.) | Size of PCR product (bp) |
|---|---|---|---|---|
| Peroxisome proliferator activated receptor gamma (PPARγ2) | forward primer | TTCGGAATCAGCTCTGTGGA | 55 | 148 |
|  | reverse primer | CCATTGGGTCAGCTCTTGTG |  |  |
| Fatty acid binding protein (aP2) | forward primer | AGCATCATAACCCTAGATGG | 55 | 128 |
|  | reverse primer | GAAGTCACGCCTTTCATAAC |  |  |
| CCAAT/ enhancer binding protein alpha (C/EBPα) | forward primer | TCGGTGCGTCTAAGATGAGG | 55 | 187 |
|  | reverse primer | TCAAGGCACATTTTTGCTCC |  |  |
| Uncouplin protein 1 (UCP1) | forward primer | GGGACCTACAATGCTTACAG | 55 | 103 |
|  | reverse primer | GGTCATATGTCACCAGCTCT |  |  |
| Uncouplin protein 3 (UCP3) | forward primer | ACGGATGTGGTGAAGGTCCG | 55 | 464 |
|  | reverse primer | TACAAACATCATCACGTTCC |  |  |
| Glyceraldehyde-3-phosphated ehydrogenase (GAPDH) | forward primer | AGAACATCATCCCTGCATCC | 55 | 321 |
|  | reverse primer | TCCACCACCCTGTTGCTGTA |  |  |

Figure 4:
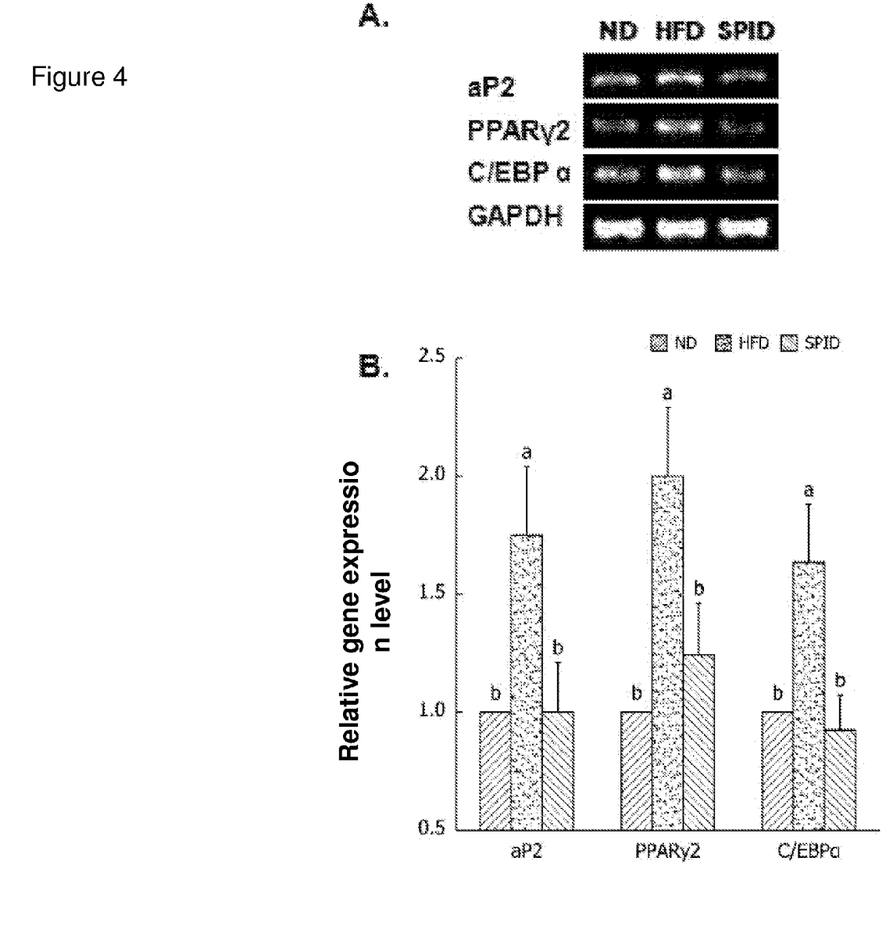
FIG. 4a shows an electrophoresis gel image of the mRNA expression levels for C/EBPα, PPARγ2 (nuclear transcription factor) and aP2 genes (their target gene)
FIG. 4b represents a graph for mRNA expression level expressed as relative values to GAPDH mRNA in ND mouse.

FIG. 4 represents the evaluating results of mRNA expression levels for C/EBPα, PPARγ2 and aP2 genes using RT-PCR. C/EBPα and PPARγ2 are nuclear transcription factors and aP2 is a target gene for these transcription factors. FIG. 4a shows an electrophoresis gel image of the mRNA expression levels for C/EBPα, PPARγ2 and aP2 genes, and FIG. 4b represents a graph for mRNA expression level expressed as relative values to GAPDH mRNA in ND mouse. In FIG. 4b, the characters above the bars indicate significant difference in dietary groups by one-way analysis of variance (ANOVA) test and Duncan's multiple range test (P<0.05). As shown in FIG. 4, the HFD group showed significantly elevated expressions of C/EBPα, PPARγ2 and aP2 genes as compared to the ND group. Nuclear transcription factors, C/EBPα and PPARγ2 play an important role in adipogenesis and aP2 is a target gene for these transcription factors. In contrast, the scopolin-fed group (SPID) showed significantly reduced expressions of C/EBPα, PPARγ2 and aP2 genes to similar levels to the ND group.

Accordingly, it would be understood that scopolin contributes to decreased expressions of nuclear transcription factors and their target gene playing a critical role in adipogenesis in visceral fat tissues, thereby suppressing the amount of visceral fats.

Figure 5:
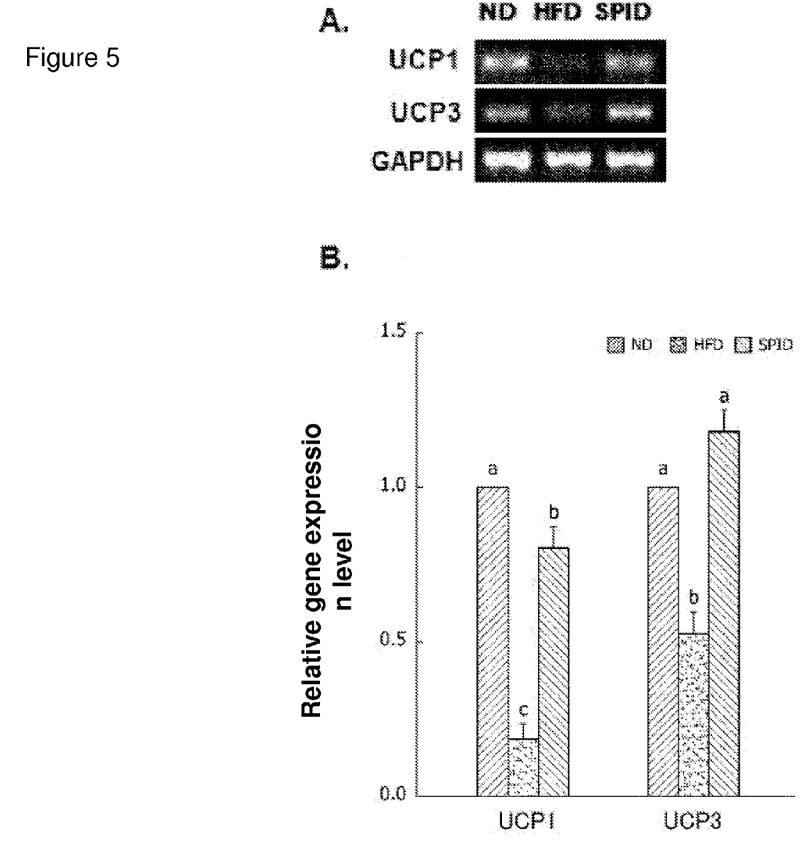
FIG. 5a shows an electrophoresis gel image of the mRNA expression levels for UCP1 and UCP3 and FIG. 5b represents a graph for mRNA expression level expressed as relative values to GAPDH mRNA in ND mouse.

Meanwhile, FIG. 5 represents the measuring results of the expression levels of UCP1 and UCP3 regulating thermogenesis in body using RT-PCR analysis. FIG. 5a shows an electrophoresis gel image of the mRNA expression levels for UCP1 and UCP3 and FIG. 5b represents a graph for mRNA expression level expressed as relative values to GAPDH mRNA in ND mouse. In FIG. 5b, the characters above the bars indicate significant difference in dietary groups by one-way analysis of variance (ANOVA) test and Duncan's multiple range test (P<0.05). As shown in FIG. 5, the expressions of UCP1 and UCP3 genes were significantly decreased in the HFD group compared with the ND group. In contrast, these HFD-induced decrease in expressions of UCP1 and UCP3 were significantly reversed by feeding scopolin to the similar level to the ND group. Therefore, it would be understood that scopolin significantly improves obesity-caused inhibition of thermogenesis in visceral fat tissues.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating obesity, fatty liver, diabetes or metabolic syndrome, comprising administrating to a mammal a therapeutically effective amount of a composition comprising an isolated or synthesized compound represented by the following Chemical formula 2:

[Chemical Formula 2]

2. The method according to claim 1, wherein the compound represented by the Chemical formula 1 is contained in an extract of a plant or its fraction; wherein the plant is one or more selected from the group consisting of *Erycibe obtusifolia, Helianthus annuus, Artemisia dalailamae, Arabidopsis thaliana, Crossostephium chinense, Santolina oblongifolia, Euphorbia chrysocoma, Diodia teres, Aesculus hippocastanum, Althaea officinalis, Apium graveolens, Artemisia abrotanum, Artemisia annua, Avena sativa, Datura stramonium, Hedera helix, Hyoscyamus niger, Ipomoea batatas, Mandragora officinarum, Morus alba, Nicotiana tabacum, Scopolia carniolica, Solanum tuberosum* and *Viburnum prunifolium*.

3. The method according to claim 1, wherein the composition is a pharmaceutical composition.

4. The method according to claim 1, wherein the composition is a food composition.

5. The method according to claim 1, wherein the composition is a health functional food composition.

6. The method according to claim 5, wherein the health functional food composition is in the form of a drink.

* * * * *